US009532809B2

(12) United States Patent
Biedermann et al.

(10) Patent No.: US 9,532,809 B2
(45) Date of Patent: Jan. 3, 2017

(54) POLYAXIAL BONE ANCHORING DEVICE

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Bernd Fischer, Braeunlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/822,618

(22) Filed: Aug. 10, 2015

(65) Prior Publication Data

US 2016/0038193 A1    Feb. 11, 2016

Related U.S. Application Data

(63) Continuation of application No. 13/673,220, filed on Nov. 9, 2012, now Pat. No. 9,131,971.
(Continued)

(30) Foreign Application Priority Data

Nov. 14, 2011    (EP) .................................... 11189054

(51) Int. Cl.
*A61B 17/04* (2006.01)
*A61B 17/86* (2006.01)
(Continued)

(52) U.S. Cl.
CPC ......... *A61B 17/7037* (2013.01); *A61B 17/685* (2013.01); *A61B 17/7032* (2013.01); *A61B 17/8605* (2013.01); *A61B 17/8685* (2013.01)

(58) Field of Classification Search
None
See application file for complete search history.

(56) References Cited

U.S. PATENT DOCUMENTS 6,736,820 B2    5/2004 Biedermann et al.
8,100,946 B2    1/2012 Strausbaugh et al.
(Continued)

FOREIGN PATENT DOCUMENTS

CN    101357073 A    2/2009
EP    1 354 563 A2    10/2003
(Continued)

OTHER PUBLICATIONS

Extended European Search Report for European Application No. 11189054.7, European Search Report dated Apr. 27, 2012 and mailed May 7, 2012 (8 pgs.).

*Primary Examiner* — Sameh Boles
(74) *Attorney, Agent, or Firm* — Lewis Roca Rothgerber Christie LLP

(57) ABSTRACT

A polyaxial bone anchoring device includes a bone anchoring element having a shank and a head, a head receiving part having a first end, an open second end, and a hollow interior portion in communication with the open second end for receiving the head therein, the head receiving part being flexible for clamping the head, a locking ring configured to be mounted around the head receiving part and having a rod receiving portion, a cap configured to be connected to the head receiving part, and a locking element configured to extend from the cap to engage an inserted rod, wherein the head is pivotable in and the cap and the locking ring are rotatable relative to the head receiving part, and wherein when the locking element is tightened, an inserted rod and an angular position of the bone anchoring element are locked relative to the head receiving part.

21 Claims, 17 Drawing Sheets

Related U.S. Application Data

(60) Provisional application No. 61/559,321, filed on Nov. 14, 2011.

(51) Int. Cl.
*A61F 2/08* (2006.01)
*A61B 17/70* (2006.01)
*A61B 17/68* (2006.01)

(56) References Cited

U.S. PATENT DOCUMENTS

| | | |
|---|---|---|
| 2003/0100904 A1 | 5/2003 | Biedermann |
| 2005/0080415 A1 | 4/2005 | Keyer et al. |
| 2007/0055242 A1 | 3/2007 | Bailly |
| 2007/0123862 A1 | 5/2007 | Warnick |
| 2007/0288004 A1* | 12/2007 | Alvarez ............. A61B 17/7032 606/86 A |
| 2009/0036934 A1 | 2/2009 | Biedermann et al. |
| 2009/0149887 A1 | 6/2009 | Schlaepfer et al. |
| 2011/0213419 A1 | 9/2011 | Richelsoph |

FOREIGN PATENT DOCUMENTS

| | | |
|---|---|---|
| EP | 2 279 706 A1 | 2/2011 |
| JP | 2002-320622 A | 11/2002 |
| JP | 2003-180707 A | 7/2003 |
| JP | 2007-508119 A | 4/2007 |
| JP | 2009-261964 A | 11/2009 |
| JP | 2011-500280 A | 1/2011 |
| JP | 2011-25037 | 2/2011 |
| WO | WO 2006/047707 A2 | 5/2006 |
| WO | WO 2009/055407 A1 | 4/2009 |

\* cited by examiner

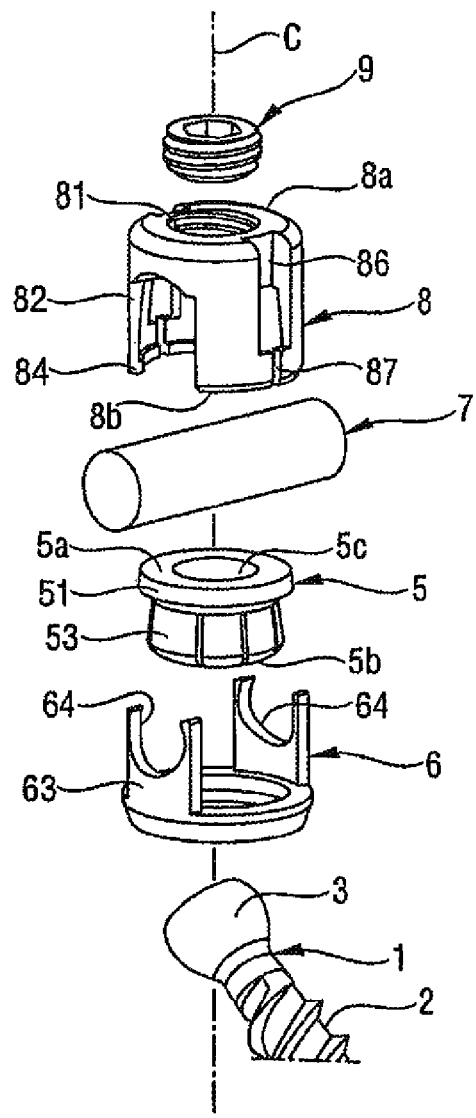
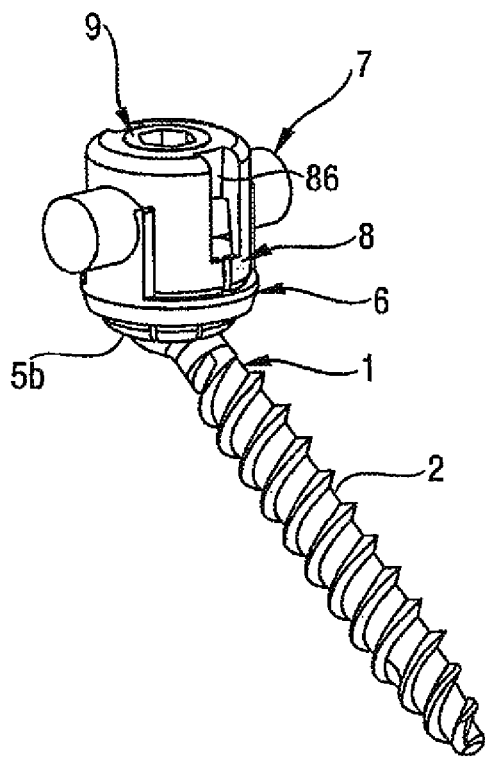
Fig. 1
Fig. 2

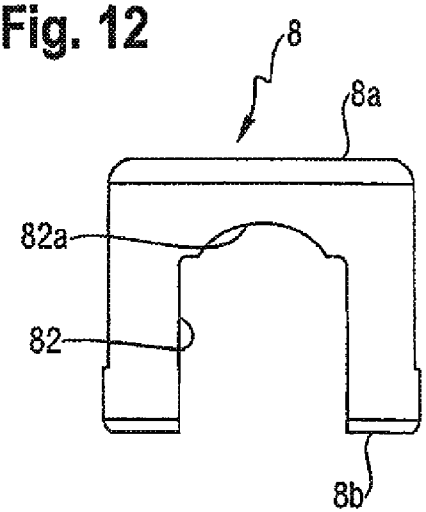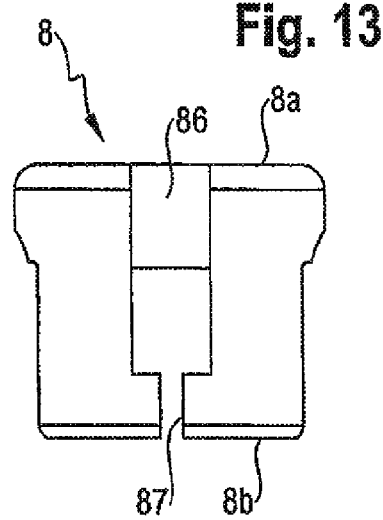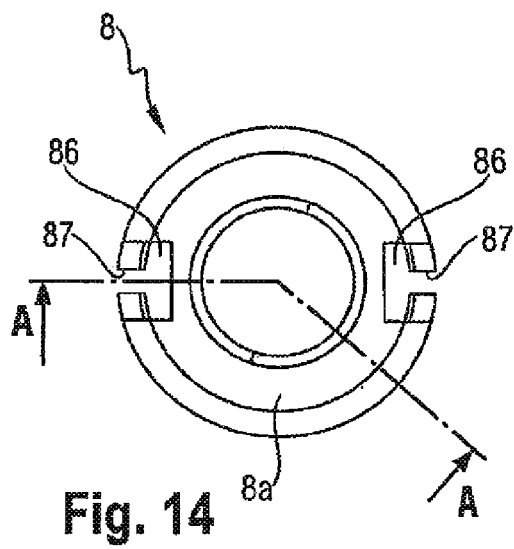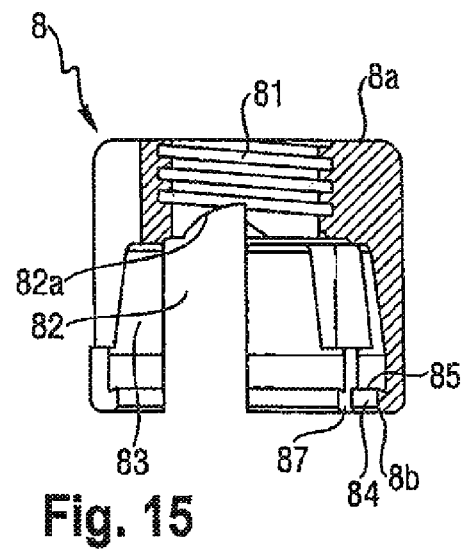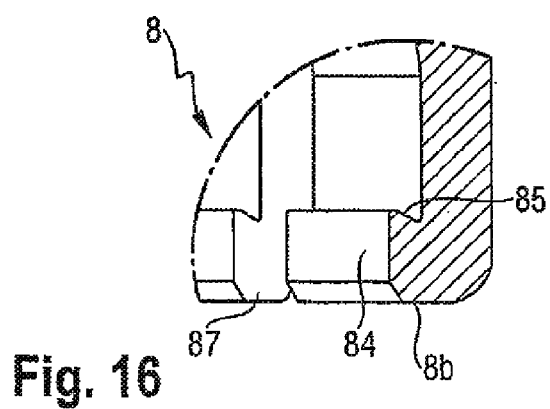

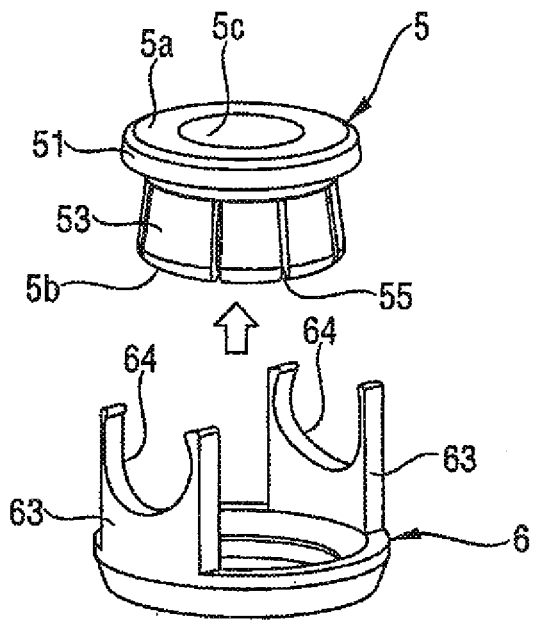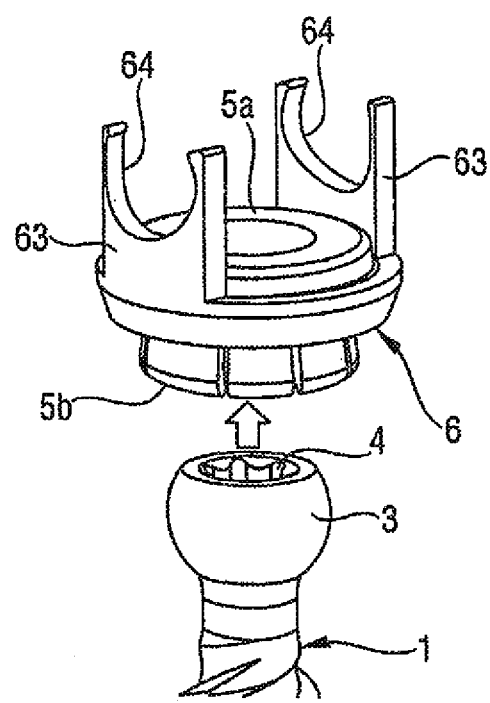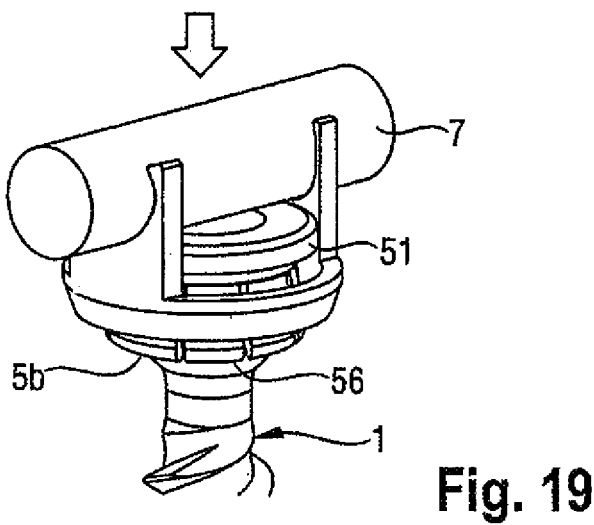
Fig. 17
Fig. 18
Fig. 19

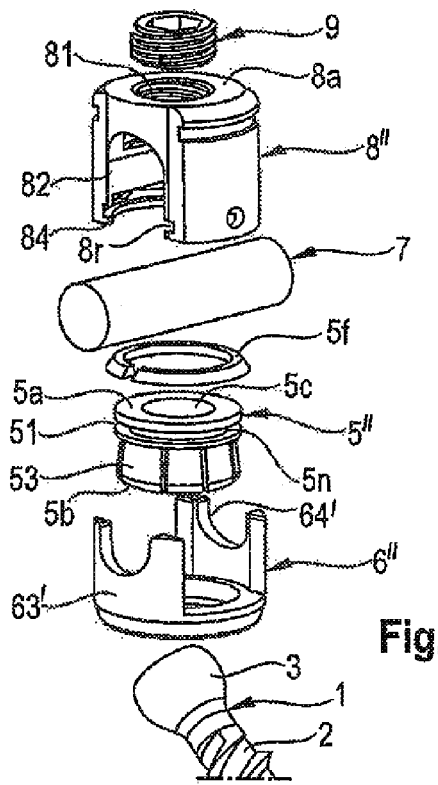
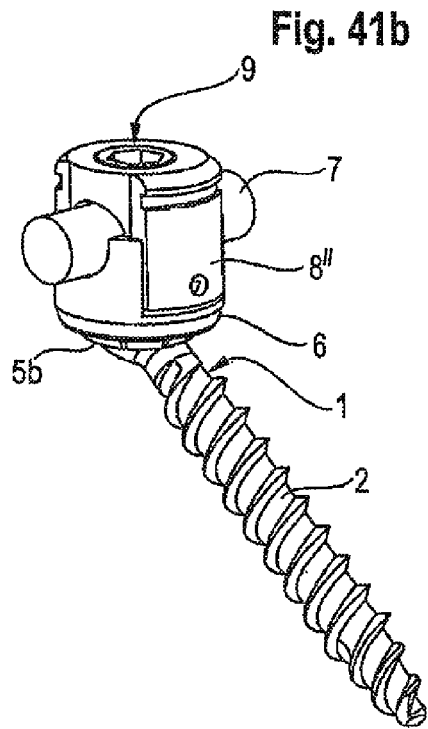
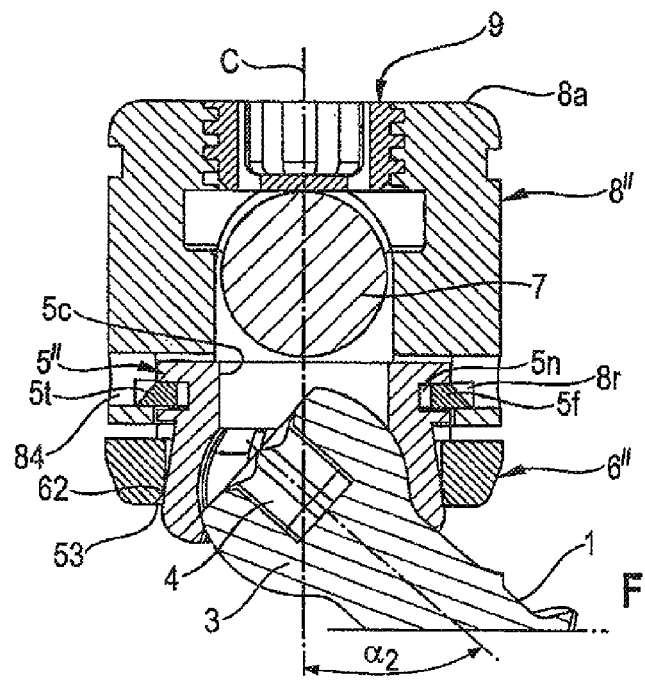
Fig. 41a
Fig. 41b
Fig. 41c

POLYAXIAL BONE ANCHORING DEVICE

CROSS-REFERENCE TO RELATED APPLICATION(S)

This application is a continuation of U.S. patent application Ser. No. 13/673,220, filed Nov. 9, 2012, which claims priority to and the benefit of U.S. Provisional Patent Application No. 61/559,321, filed Nov. 14, 2011, the contents of which are hereby incorporated by reference in their entirety. This application also claims priority to and the benefit of European Patent Application No. EP 11 189 054.7, filed Nov. 14, 2011, the contents of which are hereby incorporated by reference in their entirety.

BACKGROUND

Field of the Invention

The invention relates to a polyaxial bone anchoring device that includes a bone anchoring element for anchoring in a bone, a head receiving part for receiving a head of the bone anchoring element, a locking ring mounted around the head receiving part for coupling a stabilization rod to the head receiving part and the bone anchoring element, a cap for securing the rod, and a locking element for locking the assembly. Upon connection of the cap to the head receiving part, a sub-assembly of the locking ring, the rod, and the cap is rotatable with respect to the head receiving part. The locking element exerts pressure onto the rod to move the locking ring to a position that locks the head in the head receiving part and fixes the rod simultaneously. The polyaxial bone anchoring device is particularly suitable for providing an enlarged pivot angle for the bone anchoring element relative to the rest of the device.

Description of Related Art

A polyaxial bone anchoring device with an enlarged pivot angle is described in U.S. Pat. No. 6,736,820. This bone anchoring device includes a bone screw and a receiving part with a seat for the head of the bone screw. The screw member can be pivoted to at least one side by an enlarged angle, because the edge of the free end of the receiving part is of asymmetric construction.

Another polyaxial bone anchor is described in US 2005/0080415 A1. This bone anchor has a body member having a U-shaped channel for receiving the rod and a compressible recess for receiving a head of the anchor member such that the anchor member can initially polyaxially angulate with respect to the body member and further has a collar slideably disposed about the body member and capable of compressing the recess around the head. The lower bounding edge of the body member may include a counter-sunk region to permit increased angulation, when the anchor member is oriented toward the counter-sunk region.

US 2009/0149887 A1 describes an apparatus for connecting a bone anchor to a support rod that includes a connector body and a cap.

SUMMARY

It is an object of embodiments of the invention to provide a polyaxial bone anchoring device that has a low profile, and in addition, a device that permits a bone anchoring element to pivot at an enlarged angle in a specific direction relative to the rest of the device.

The polyaxial bone anchoring device according to embodiments of the invention makes use of a cap and a locking element received in the cap for securing and fixing a rod and a head of the bone anchoring element relative to the rest of the device. Therefore, splaying of portions of a receiving part when tightening a locking element, as may be the case in conventional receiving parts, does not occur. Furthermore, with the cap according to embodiments of the invention, the bone anchoring device can have a lower profile in an axial or height direction of the bone anchoring device.

With the polyaxial bone anchoring device according to embodiments of the invention, a modular screw system can also be provided. The modular system may include a head receiving part preassembled with a locking ring, the cap preassembled with the locking element, and a set of bone anchoring elements having different shanks or other properties. By means of this, various shanks with different diameters, thread forms, or other different features can be combined with the head receiving part and locking ring, according to the requirements of a particular clinical situation. In a further modular system, different head receiving parts with different bounding edges for allowing different maximum pivot angles may be provided, that can be selectively assembled with a locking ring, a cap with locking element and various shanks. Therefore, a surgeon or other practitioner can have a wider choice of implants and combinations. By such modularity, costs of stock-holding can be decreased.

When the head receiving part has a free bounding edge that is configured to permit an inserted bone anchoring element to pivot at a larger pivot angle at a first location of the bounding edge than at a second location of the bounding edge, the pivot angle can be selected within a range of 360° around a central axis of the locking ring or cap of the device. A maximum pivot angle of the bone anchoring element relative to the head receiving part may be equal to or greater than 45° measured from a straight position. An orientation of the enlarged pivot angle can be selected, for example, in a plane including the rod axis, at 90° with respect to the rod axis, or at any other angle in between. This renders the bone anchoring device particularly suitable for applications such as lateral mass fixation, for example, for the cervical spine.

The design of the bone anchoring device according to embodiments of the invention may allow for reduced dimensions in terms of height as well as in terms of diameter when compared to previous bone anchoring devices, which may make it particularly suitable for applications where small-sized anchoring devices are required or desirable, such as in the fields of cervical spine surgery or pediatric applications, trauma, and minimally invasive applications for bone surgery.

BRIEF DESCRIPTION OF THE DRAWINGS

Further features and advantages will become apparent from the descriptions of embodiments by means of the accompanying drawings. In the drawings:

FIG. 1 shows an exploded perspective view of a polyaxial bone anchoring device according to a first embodiment;

FIG. 2 shows a perspective view of the polyaxial bone anchoring device of FIG. 1 in an assembled state;

FIG. 12 shows a side view of the cap of FIGS. 10 and 11;

FIG. 13 shows another side view of the cap in FIG. 12, rotated by 90°;

FIG. 14 shows a top view of the cap of FIGS. 10 and 11;

FIG. 15 shows a cross-sectional view of the cap of FIG. 14, the sections taken along line A-A in FIG. 14;

FIG. 16 shows an enlarged view of a portion of FIG. 15;

FIGS. 17 to 21 show steps of assembly and use of the polyaxial bone anchoring device according to the first embodiment;

FIG. 41a shows an exploded perspective view of an assembly of a polyaxial bone anchoring device according to yet a further embodiment;

FIG. 41b shows the bone anchoring device of FIG. 41a in an assembled state;

FIG. 41c shows a cross-sectional view of the bone anchoring device of FIGS. 41a and 41b, the section being taken in a plane perpendicular to an axis of an inserted rod;

FIG. 42c shows a perspective view from a top of the head receiving part of FIG. 42a;

DETAILED DESCRIPTION

Figure 3:
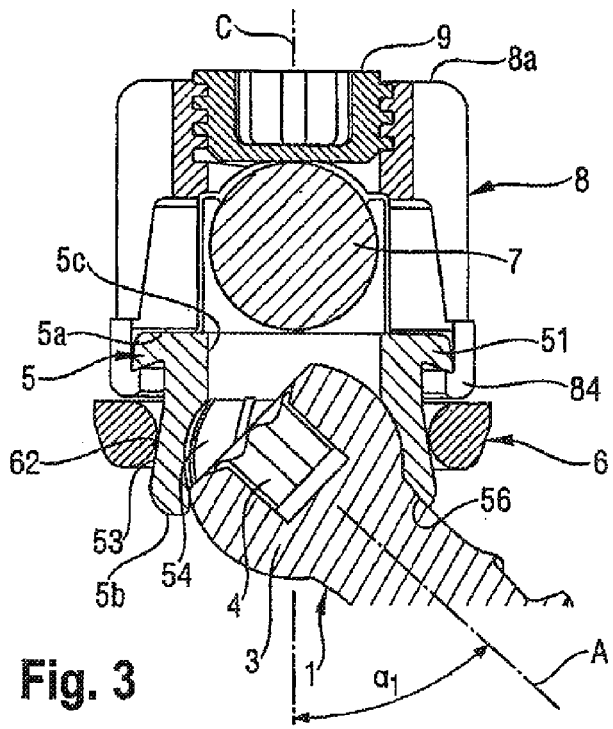
FIG. 3 shows a cross-sectional view of the polyaxial bone anchoring device of FIGS. 1 and 2 in a first pivot position of a bone anchoring element, the section taken perpendicular to an axis of an inserted rod.

As shown in FIGS. 1 to 5, a polyaxial bone anchoring device according to a first embodiment includes a bone anchoring element 1 in the form of a bone screw having a shank 2 with a threaded section and a spherical segment-shaped head 3. The head 3 has a recess 4 for engagement with a tool. The bone anchoring device further includes a head receiving part 5 for receiving the head 3 of the bone anchoring element 1, and a locking ring 6 for receiving a rod 7, for example a spinal stabilization rod, and for connecting the rod 7 to the bone anchoring element 1. In addition, the bone anchoring device includes a cap 8 for securing the rod 7 and a locking element 9 in the form of a set screw for locking the rod 7 and the head 3 relative to the rest of the bone anchoring device.

Figure 6:
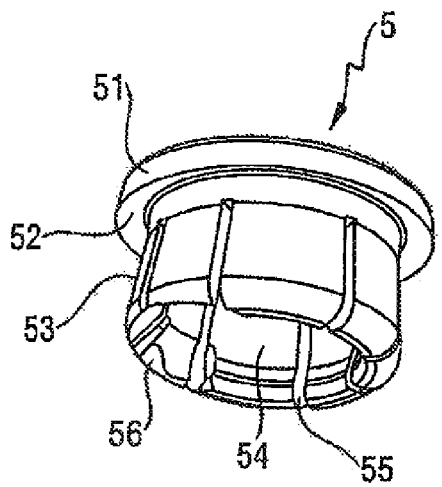
FIG. 6 shows a perspective view of a head receiving part of the polyaxial bone anchoring device according to the first embodiment.
Figure 7:
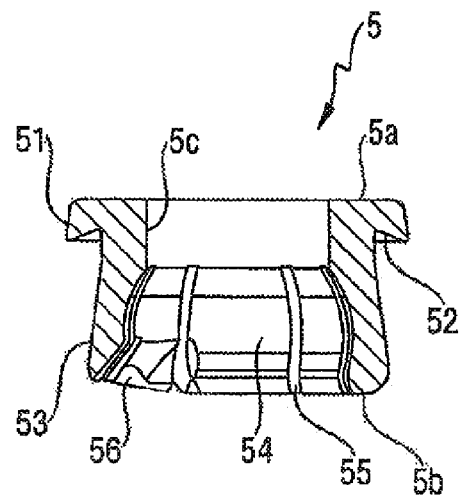
FIG. 7 shows a cross-sectional view of the head receiving part shown in FIG. 6.

Referring in particular to FIGS. 6 and 7, the head receiving part 5 has a first end 5a, an opposite second end 5b, and a coaxial through hole 5c. Adjacent to the first end 5a is a substantially outwardly extending rim portion 51. The rim portion 51 has on a side facing away from the first end 5a a circumferentially extending undercut portion 52. The undercut portion 52 is formed by a surface that is inclined outwards and towards the second end 5*b*. The undercut portion 52 serves for engagement with a portion of the cap 8.

The head receiving part 5 further includes a conically-shaped outer surface portion 53 that widens towards the second end 5*b*. A maximum outer diameter of the head receiving part at the second end 5*b* is smaller than a diameter of rim portion 51 at the first end 5*a*. An internal hollow spherical section 54 forming an accommodation space for the spherical segment-shaped head 3 of the bone anchoring element 1 is formed in the head receiving part 5. The internal hollow spherical section 54 is configured to encompass the head 3 of the bone anchoring element 1 from the side, covering a region including a largest diameter of the head 3.

A plurality of slits 55 are provided that are open to the second end 5*b*. The slits 55 extend substantially through a wall of the internal hollow portion 54 and render the head receiving part 5 flexible in a region where the head 3 is received. By the size and number of the slits, a desired elasticity can be provided to the head receiving part 5. The elasticity of the head receiving part 5 is such that the head 3 of the anchoring element 1 can be inserted by expanding the head receiving part 5, and can be clamped by compressing the head receiving part 5.

An edge bounding the second end 5*b* may be asymmetric. In the embodiment shown, this is achieved by a countersunk or recessed area 56 provided in the wall of the internal hollow space 54. By means of this, the anchoring element 1 can pivot at the position of the recessed area 56 to a larger pivot angle $\alpha_1$, with respect to a straight position when an anchor axis A of the anchoring element 1 is coaxial with a central axis C of the head receiving part 5, as shown in FIG. 3, compared to a smaller pivot angle $\alpha_2$ in the opposite direction, FIG. 4, or at various other positions. The recessed area 56 defines the position of the enlarged pivot angle with respect to the locking ring 6, as described further below.

Figure 8:
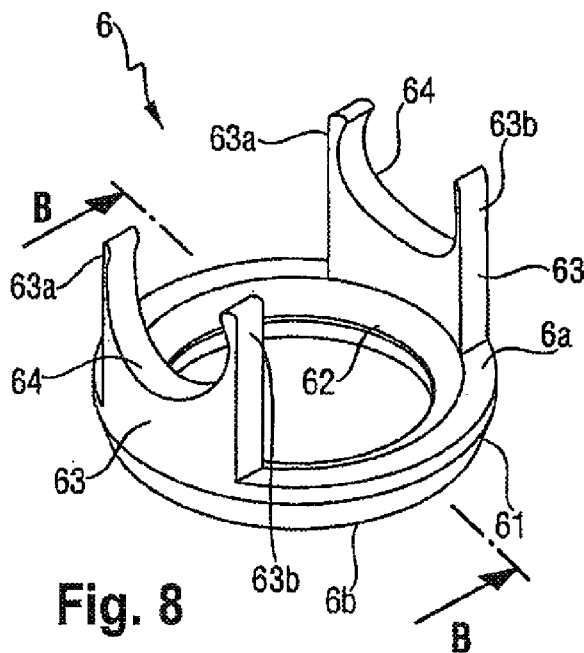
FIG. 8 shows a perspective view of a locking ring of the polyaxial bone anchoring device according to the first embodiment.
Figure 9:
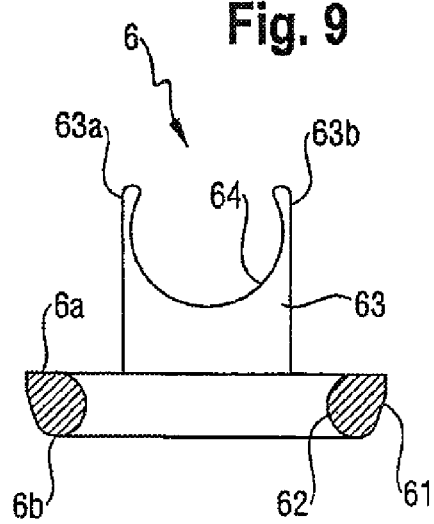
FIG. 9 shows a cross-sectional view of the locking ring of FIG. 8, the section taken along line B-B in FIG. 8.
Figure 10:
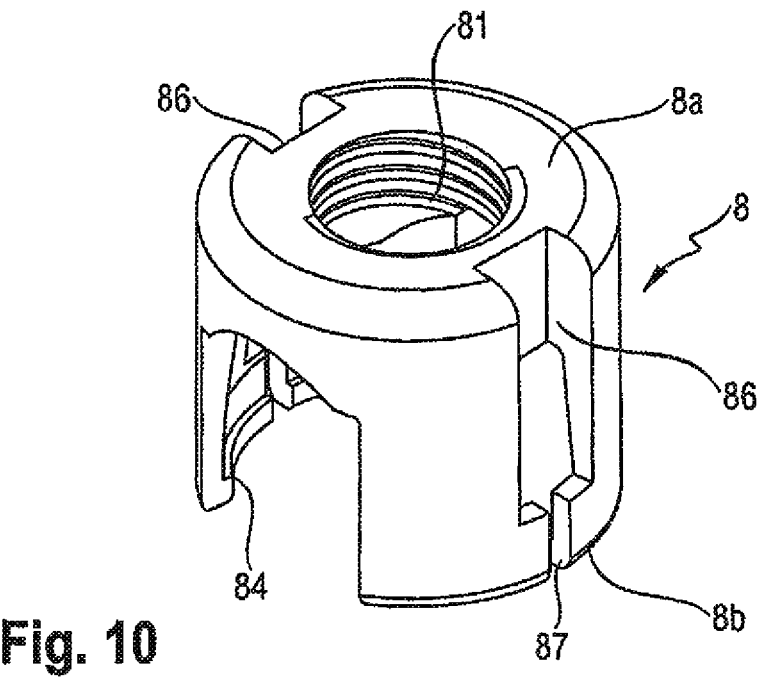
FIG. 10 shows a perspective view from a top of a cap of the polyaxial bone anchoring device according to the first embodiment.
Figure 11:
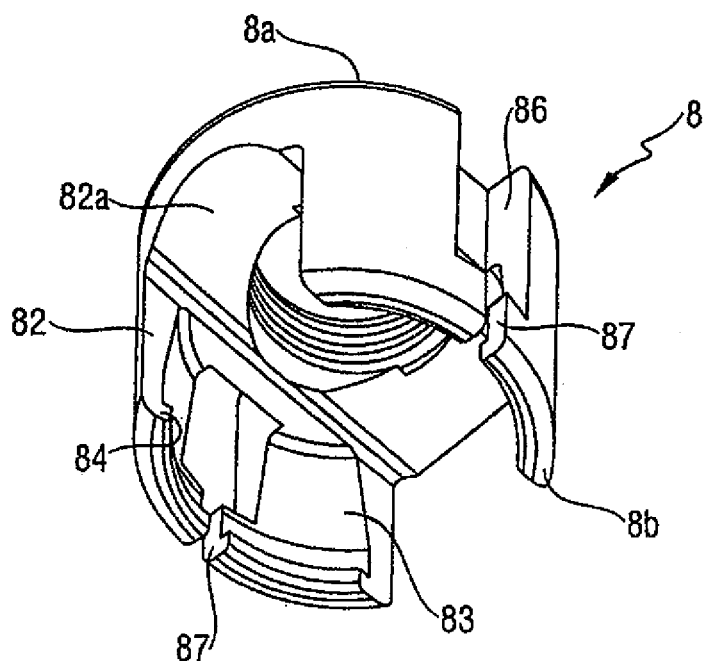
FIG. 11 shows a perspective view from below of the cap of the bone anchoring device of FIG. 10.

The locking ring 6 is shown in more detail in FIGS. 8 and 9. The locking ring 6 may be a slightly conical outer surface portion 61, and at its inner side a curved internal surface portion 62. The curvature of portion 62 is directed towards a center of the locking ring 6. The curved surface portion 62 can have a semi-circular cross-section, but other types of curvatures are also possible. An inner diameter of the locking ring 6 is such that the locking 6 can slide along the outer conical surface portion 53 of the head receiving part 5, thereby compressing the head receiving part 5 in an increasing manner when sliding downwards (i.e., towards second end 5*b*).

On a side facing the rim portion 51 of the head receiving part 5 when assembled, the locking ring 6 includes two projections 63 located diametrically opposite to each other. The projections 63 have a height such that they project up and away from the first end 5*a* of the head receiving part 5 when the locking ring 6 is mounted around the head receiving part 5, as depicted, for example, in FIG. 18. At their free ends, the projections 63 each has a recess 64 that has a shape of a segment of a circle, including at least a portion with a greatest diameter of said circle. A diameter of the circular segment-shaped recess 64 corresponds substantially to a diameter of the rod 7. By means of the recess 64, each projection 63 forms two upstanding legs 63*a*, 63*b* that allow the rod 7 to be clicked and held between them.

The flexibility of the head receiving part 5 and the size of the head receiving part 5 at the open second end 5*b* allows mounting of the locking ring 6 from the second end 5*b*. When the locking ring 6 is mounted onto the head receiving part 5, the locking ring 6 is freely rotatable around the head receiving part 5. The dimensions of the respective parts can be designed such that the head 3 may be preliminarily held in the head receiving part 5 by a slight friction force, and the locking ring 6 may also be held by a friction force in a preliminary manner around the head receiving part 5.

The cap 8 will now be described with reference to FIGS. 10 to 16. The cap 8 is substantially cylindrical, with a first end 8*a* and a second end 8*b*. At the first end 8*a*, there is a coaxial threaded through hole 81 for receiving the locking element 9. At the second end 8*b*, there is a substantially cuboid-shaped or rectangular-shaped recess 82, that continues into a cylindrical recess 82*a* having a cylinder axis extending perpendicular to the axis of the threaded through hole 81. A depth of the recess 82 and 82*a* is such that the rod 7 can be covered by the recesses 82 and 82*a* while the cap 8 is mounted to the head receiving part 5.

At the second end 8*b*, the cap 8 further includes a coaxial substantially conical segment-shaped recess 83. By means of the recess 83, a wall thickness of the cap 8 decreases towards the second end 8*b* in this region. An inwardly projecting rim 84 is provided at the second end 8*b* that has an undercut portion 85 with an inclined surface, wherein the inclination substantially corresponds to the inclination of the undercut portion 52 of the head receiving part 5. A size of the rim 84 with the undercut portion 85 is such that the rim 84 can engage the undercut portion 52 at the rim portion 51 of the head receiving part 5.

The cap 8 further includes two engagement portions 86 for holding, mounting, or removal of the cap 8 from the head receiving part 5 with a tool. The engagement portions 86 extend from the first end 8*a* to a distance from the second end 8*b*, and are each located at 90° with respect to the rod receiving recesses 82, 82*a*. The engagement portions 86 are formed as recessed portions configured to be engaged with a tool. A wall thickness of the cap at the engagement portions 86 may be reduced. At the positions of the engagement portions 86, the cap has slits 87, respectively, which extend from the respective engagement portion 86 to the second end 8*b*, completely through a wall of the cap 8. By means of the slits 87, wall portions of the cap 8 are flexible to some extent, so as to allow mounting of the cap 8 to the head receiving part 5, in such a way that the rim 84 of the cap 8 snaps behind the rim 51 of the head receiving part 5.

The locking element 9, in the form of a set screw, is configured to be screwed into the threaded through hole 81. Although the thread is shown to be a flat thread, any other thread form, such as a metric thread, can be used.

The head receiving part 5, the locking ring 6, the cap 8, and the locking element 9, as well as the bone anchoring element 1, are made of a bio-compatible material, for example, of titanium or stainless steel, of bio-compatible alloys, such as nickel-titanium alloys, for example, Nitinol, or of a bio-compatible plastic material, such as, for example, polyether ether ketone (PEEK). The parts can be made of the same or of different materials.

Referring to FIGS. 17 to 21, steps of mounting and use of the polyaxial bone anchoring device will be explained. As shown in FIG. 17, the locking ring 6 is mounted from the second end 5*b* to the head receiving part 5 such that, as shown in FIG. 18, the projections 63 for receiving the rod 7 extend upwards from the first end 5*a* of the head receiving part 5. In some embodiments, the head receiving part 5 and the locking ring 6 may be delivered in a pre-assembled manner. In a second step shown in FIG. 18, the bone anchoring element 1 with a suitable shank 2 for a specific clinical application is mounted from the second end 5*b* to the assembly formed by the head receiving part 5 and the locking ring. The locking ring 6 may be in its uppermost position relative to the head receiving part 5, where its first end 6a abuts against the rim portion 51 of the head receiving part 5. The head 3 is introduced into the internal hollow section 54 of the head receiving part 5. This is possible because the head receiving part 5 is flexible.

Here, the modularity of the bone anchoring device allows for combining of a specific bone anchoring element having a specific shank with the head receiving part 5 during or before surgery. When the head receiving part 5 and locking ring 6 are mounted together, they are still rotatable with respect to each other. Therefore, a position of the recessed area 56 can be freely selected by rotating the head receiving part 5 with respect to the locking ring 6. Hence, by providing different head receiving parts with different predefined maximum pivot angles, which can be combined with different bone anchoring element having different shanks, a more suitable bone anchoring device can be selected and assembled more easily.

The polyaxial bone anchoring device thus assembled is then inserted into a bone or a vertebra. In an alternative way of use, the bone anchoring element 1 is first inserted into the bone or vertebra, and thereafter the combination of the head receiving part 5 and the locking ring 6 is mounted to the head 3 after implantation of the bone anchoring element 1.

Then, as shown in FIG. 19, the rod 7 is inserted into the recesses 64 provided at the projections 63. Because the recesses 64 have circular segment shapes including largest diameters of the circles, the rod 7 can be clicked into the recesses 64 so that the rod 7 is preliminarily held in place therein. The assembly including the rod 7 and the locking ring 6 is still rotatable with respect to the head receiving part 5 in this position.

Figure 20:
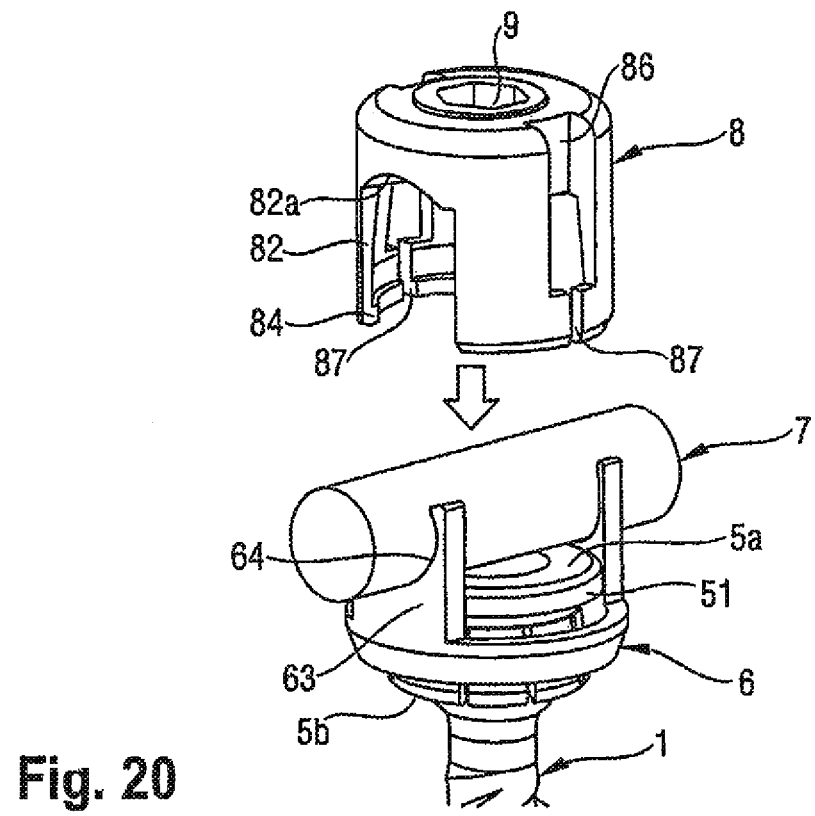

In a next step, as shown in FIG. 20, the cap 8 with the locking element 9 inserted therein is placed onto the rest of the assembly. Because wall sections of the cap 8 are slightly flexible, the cap 8 can be clicked onto the head receiving part 5, so that the rim portion 84 snaps behind or under the rim portion 51 of the head receiving part 5, and the undercut portions 52 and 85 engage each other. This is shown in detail in FIG. 5.

Figure 21:
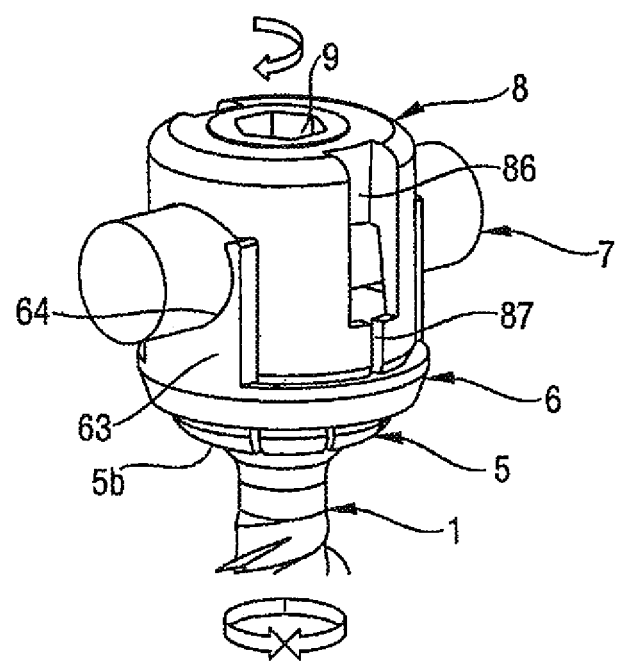
Figures 22, 23:
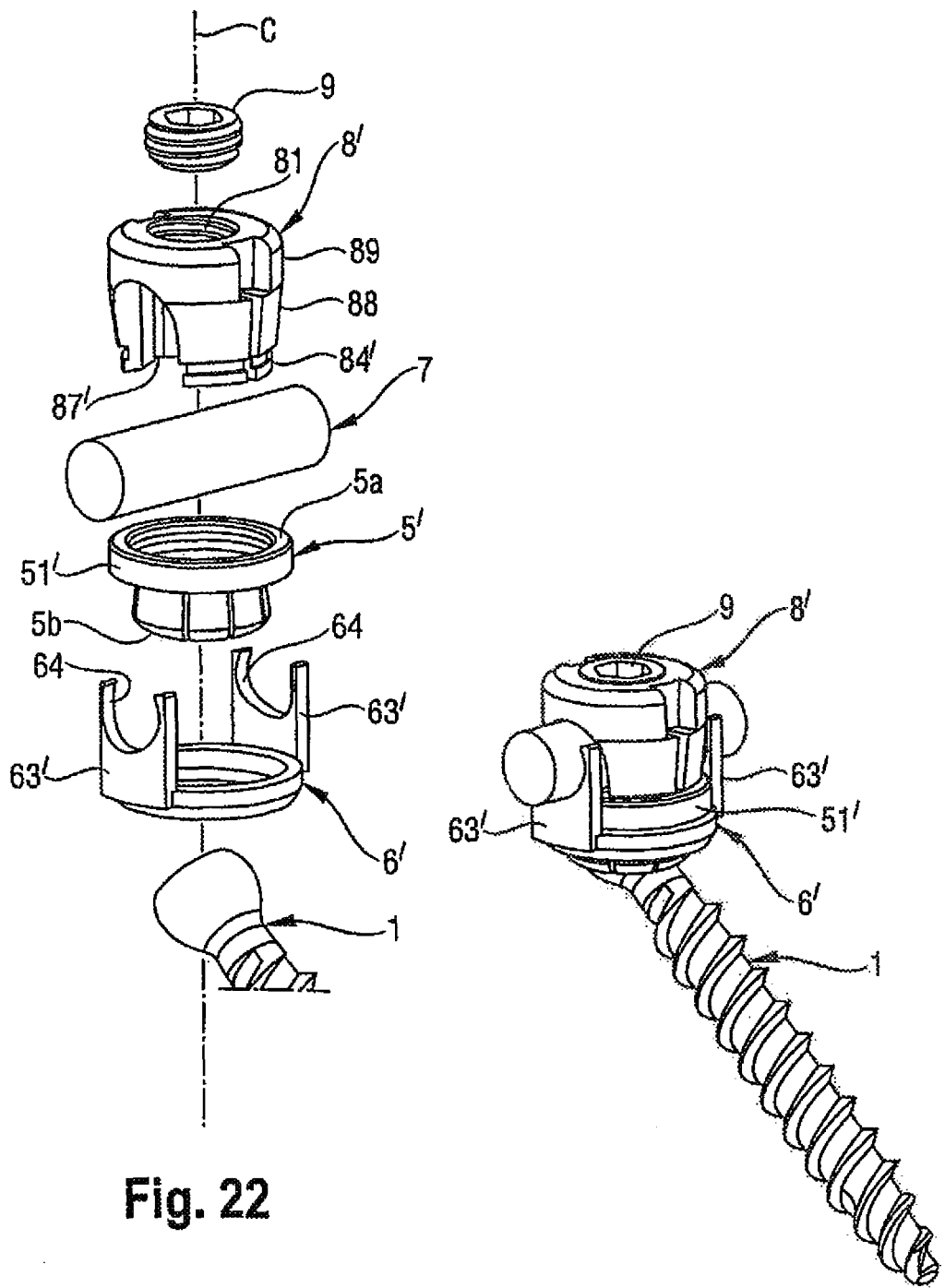
FIG. 22 shows an exploded perspective view of a polyaxial bone anchoring device according to a second embodiment.
FIG. 23 shows a perspective view of the polyaxial bone anchoring device of FIG. 22 in an assembled state.
Figure 24:
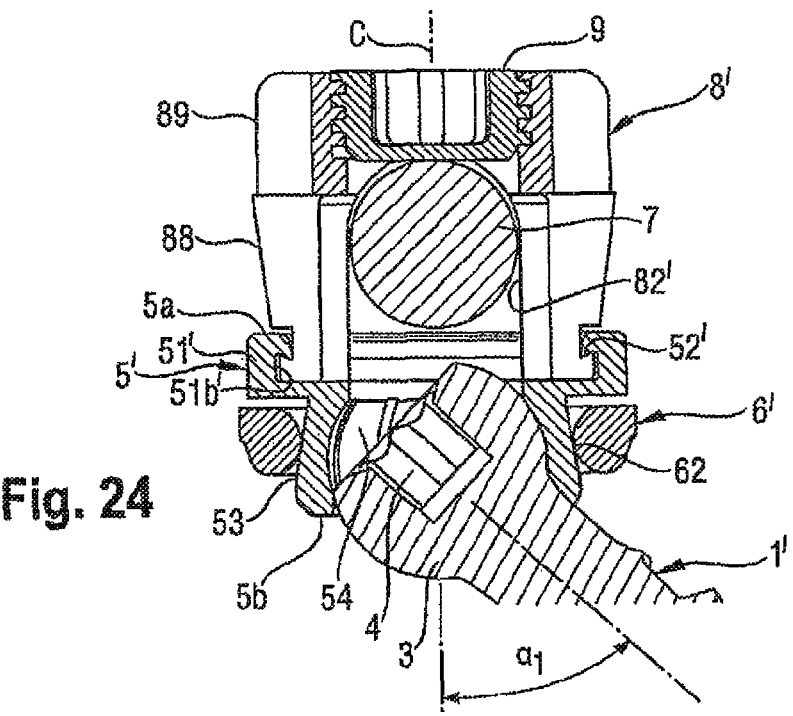
FIG. 24 shows a cross-sectional view of the polyaxial bone anchoring device according to the second embodiment in a first pivot position of a bone anchoring element, the section taken perpendicular to an axis of an inserted rod.
Figure 25:
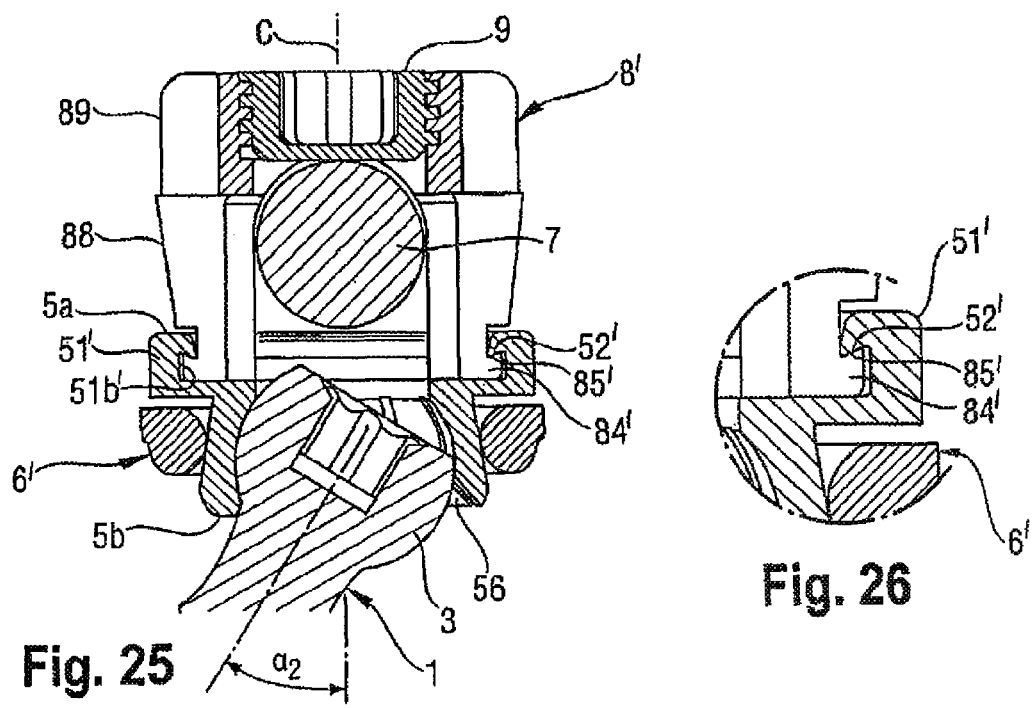
FIG. 25 shows a cross-sectional view of the polyaxial bone anchoring device of the second embodiment in a second pivot position of the bone anchoring element, the section taken perpendicular to the rod axis.
Figure 26:
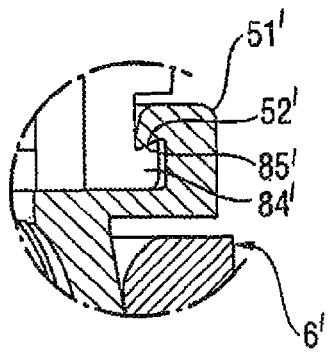
FIG. 26 shows an enlarged view of a portion of FIG. 25.
Figure 27:
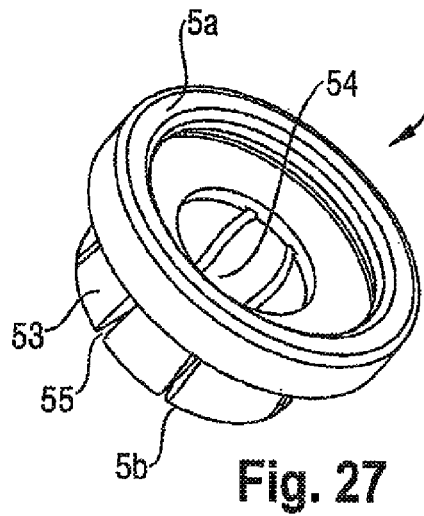
FIG. 27 shows a perspective view from a top of a head receiving part of the polyaxial bone anchoring device according to the second embodiment.
Figure 28:
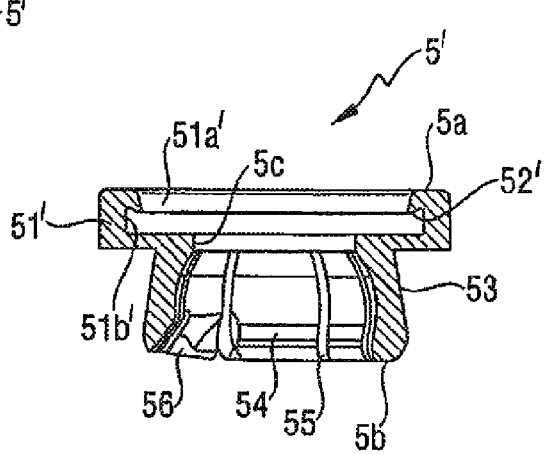
FIG. 28 shows a cross-sectional view of the head receiving part of FIG. 27.

Finally, as shown in FIG. 21, the locking element 9 in the form of the set screw is tightened until its lower side presses onto the rod 7. As a consequence thereof, the rod 7 presses the locking ring 6 downward to compress the head receiving part 5. Final tightening of the locking element 9 locks the rod 7 and the head 3 simultaneously.

Figures 4, 5:
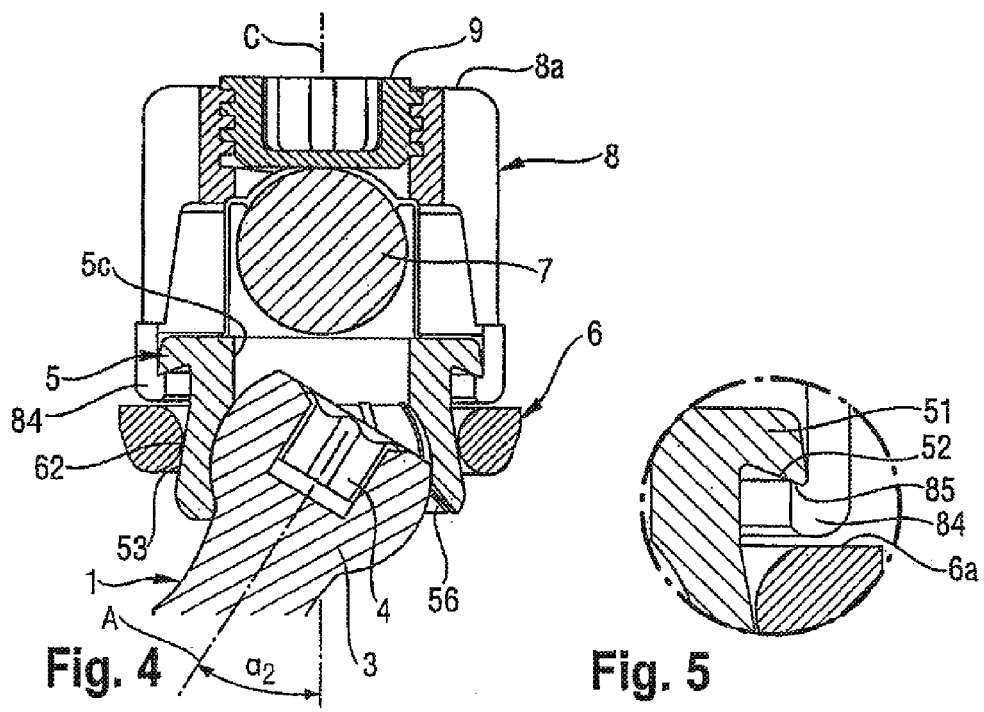
FIG. 4 shows a cross-sectional view of the polyaxial bone anchoring device in a second pivot position of the bone anchoring element, the section taken perpendicular to the rod axis.
FIG. 5 shows an enlarged view of a portion of FIG. 4.

Referring to FIGS. 3 and 4, the bone anchoring element 1 can assume a position with a largest pivot angle $\alpha_1$ with respect to the central axis C of the device when the bone anchoring element 1 is pivoted to the side including the recessed area 56 (FIG. 3). Meanwhile, as shown in FIG. 4, the bone anchoring element 1 can also assume a second pivot position in the opposite direction, or in any other direction, with a pivot angle $\alpha_2$ that is smaller than $\alpha_1$.

A second embodiment of a polyaxial bone anchoring device will be described with reference to FIGS. 22 to 37. Parts and portions that are identical or similar to the parts and portions of the first embodiment are designated with the same reference numerals, and the descriptions thereof shall not be repeated. The bone anchoring device according to the second embodiment differs from the bone anchoring device according to the first embodiment in the design of the head receiving part, the locking ring, and the cap.

As shown in particular in FIGS. 22 to 28, a head receiving part 5' includes a rim 51' extending beyond a second end 5b seen in a radial direction. Adjacent to a first end 5a, a recess 51a' is provided with an inner diameter that may also be greater than the outer diameter of the head receiving part 5 at the second end 5b. Furthermore, a groove 51b' is provided with an undercut portion 52' facing away from the first end 5a. The groove 51b' and the undercut portion 52' serve for engagement with a portion of a cap 8'.

Figure 29:
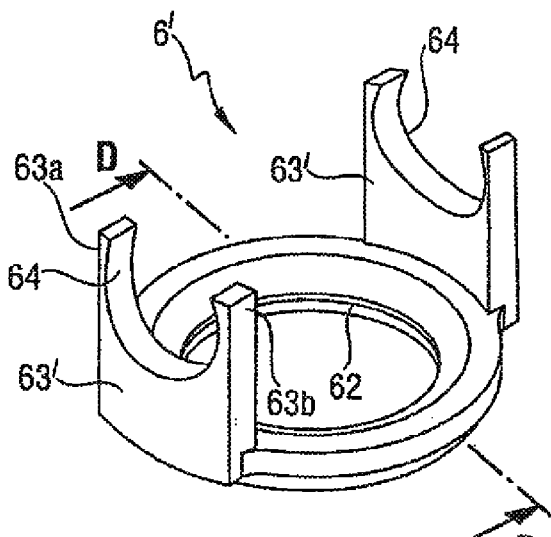
FIG. 29 shows a perspective view of a locking ring of the polyaxial bone anchoring device according to the second embodiment.
Figure 30:
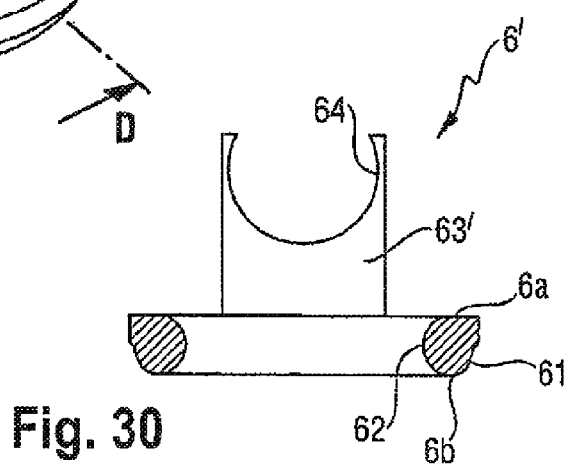
FIG. 30 shows a cross-sectional view of the locking ring of FIG. 29, the section taken along line D-D in FIG. 29.
Figure 31:
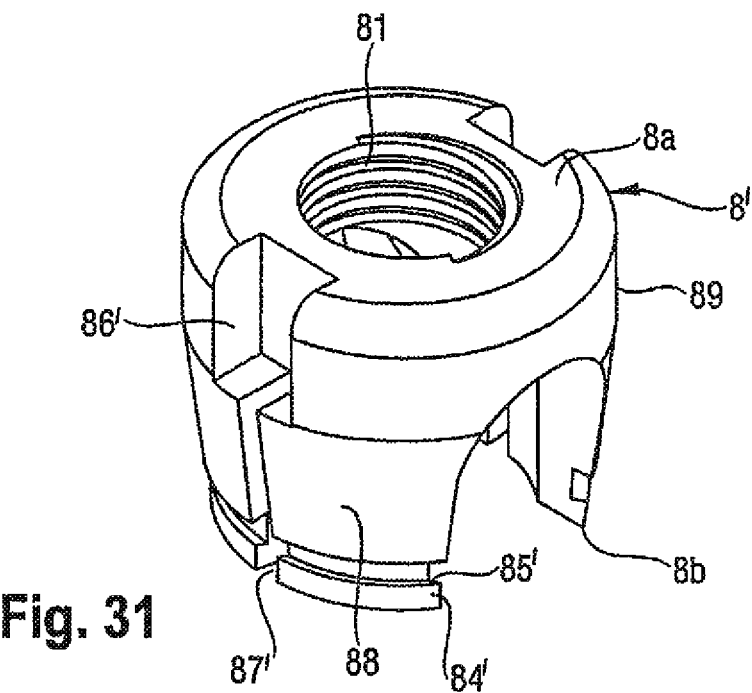
FIG. 31 shows a perspective view from a top of a cap of the polyaxial bone anchoring device according to the second embodiment.
Figure 32:
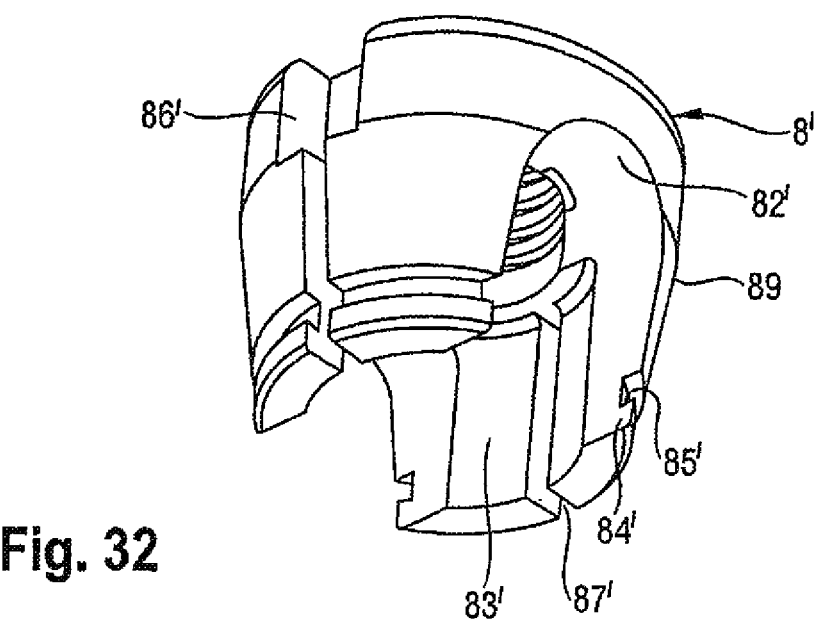
FIG. 32 shows a perspective view of the cap of the polyaxial bone anchoring device according to the second embodiment from below.
Figure 33:
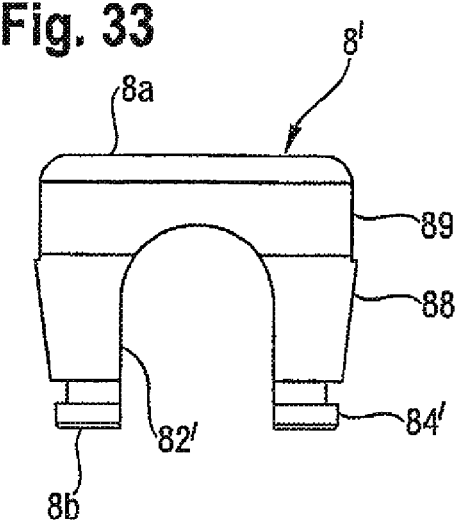
FIG. 33 shows a side view of the cap of FIGS. 31 and 32.
Figure 34:
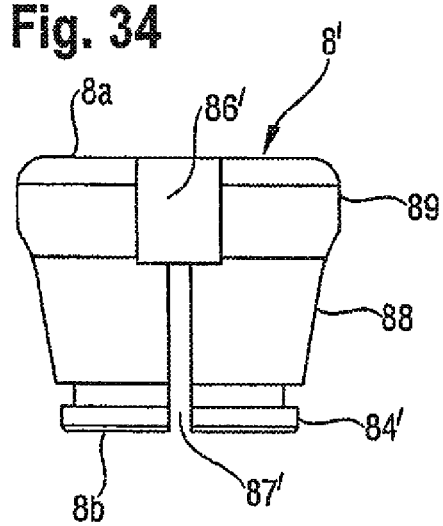
FIG. 34 shows another side view of the cap of FIG. 33, rotated by 90°.
Figure 35:
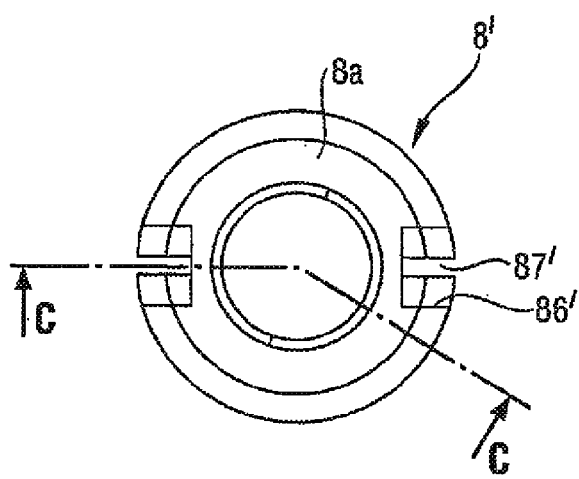
FIG. 35 shows a top view of the cap of FIGS. 31 and 32.
Figure 36:
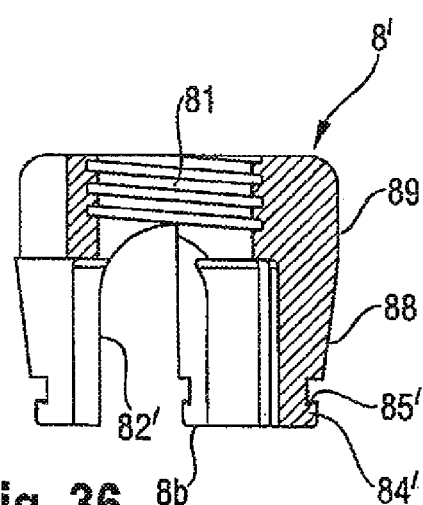
FIG. 36 shows a cross-sectional view of the cap of FIG. 35, the section taken along line C-C in FIG. 35.
Figure 37:
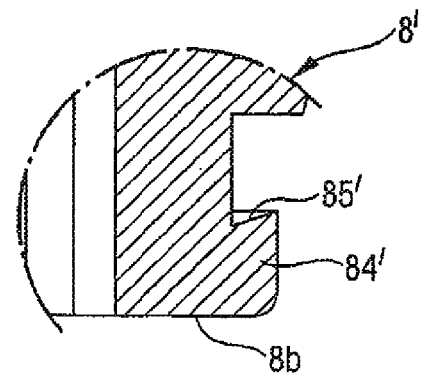
FIG. 37 shows an enlarged view of a part of FIG. 36.

As shown in FIGS. 29 and 30, a locking ring 6' has rod receiving projections 63' that are placed at an outer circumference of the locking ring 6'. Here, a height of the projections 63' projecting above the head receiving part 5' is smaller, and the cap 8' can be made shorter compared to the previous embodiment, so that the bone anchoring device as a whole may have a lower profile in an axial direction.

With reference to FIGS. 31 to 37, the cap 8' has adjacent a second end 8b an outwardly projecting rim 84' with an undercut portion 85' with an inclined surface configured to cooperate with undercut portion 52' of the head receiving part 5'. Furthermore, the cap 8' has a slightly conically segment-shaped outer surface portion 88 adjacent the second end 8b, and including the rim portion 84', where the conical portion 88 is connected to a cylindrical segment-shaped portion 89. Inside, the cap 8' has a cylindrical bore 83'. In the region of the conical outer surface portion 88, a wall thickness of the cap 8' slightly decreases towards the second end 8b. Engagement portions 86' for a tool may extend only into the cylindrical portion 89. Meanwhile, slits 87' extend completely through the conical outer surface portion 88 so as to render the cap 8' flexible in this region. Furthermore, a recess 82' for receiving the rod is U-shaped. The other parts of cap 8' are the same as or similar to the cap 8 in the first embodiment. Assembly and use of the bone anchoring device according to the second embodiment is similar to that of the first embodiment, with a main difference shown in FIGS. 24 to 26 where, the cap 8' is clicked and attached to an inside of the head receiving part 5' into the groove 51b' of the head receiving part 5'.

Figure 38:
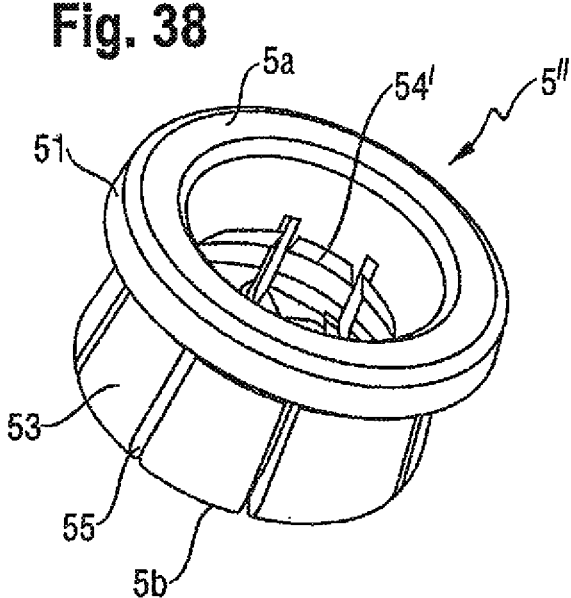
FIG. 38 shows a perspective view from a top of a head receiving part of a polyaxial bone anchoring device according to a third embodiment.
Figure 39:
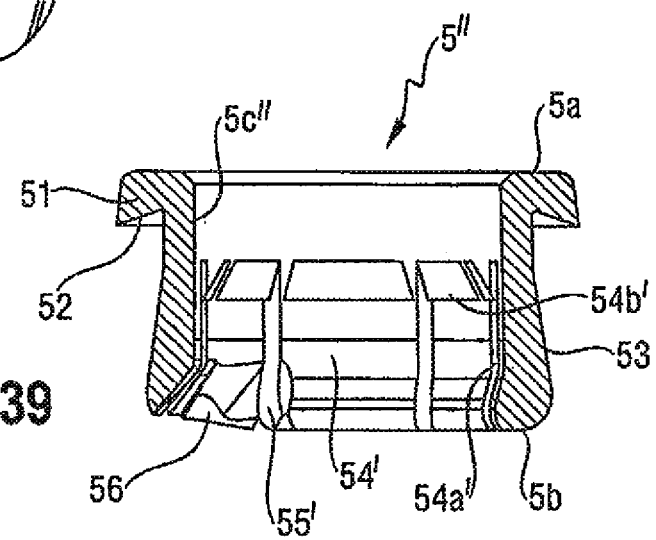
FIG. 39 shows a cross-sectional view of the head receiving part shown in FIG. 38.
Figure 40:
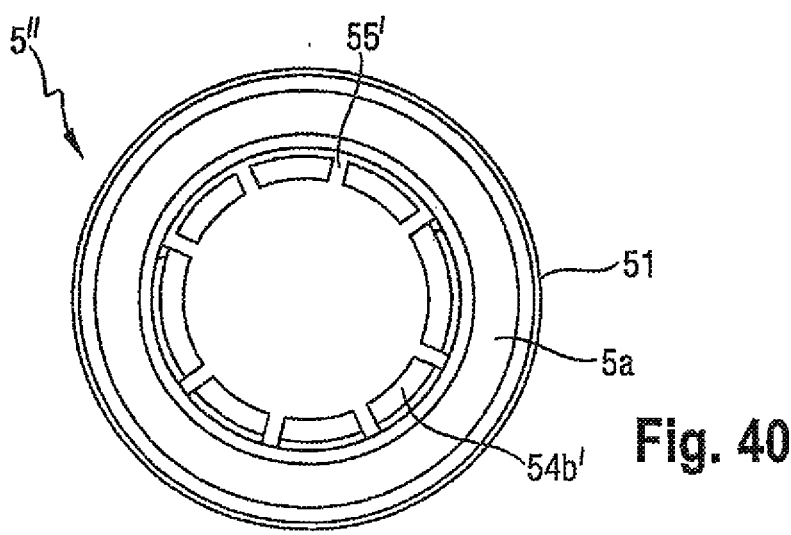
FIG. 40 shows a top view of the head receiving part of FIG. 38.

With reference to FIGS. 38 to 40, a third embodiment of the polyaxial bone anchoring device differs from the bone anchoring device according to the first embodiment in the design of the head receiving part. A head receiving part 5" has an axial through hole 5c" extending from a first end 5a in a direction of a second end 5b, with a diameter larger than the diameter of the head 3, to allow the head 3 to pass therethrough. A hollow interior section 54' includes a first spherically-shaped portion 54a' forming a seat for the head 3, and a second narrowing portion 54b' at a side opposite to the second end 5b that narrows towards the first end 5a, so that the portion 54b' forms an obstacle for the head 3. Slits 55' extend fully into the second portion 54b'. Hence, with the head receiving part 5", a top loading bone anchoring device is provided which allows insertion of the bone anchoring element 1 from the first end 5a through the axial through hole 5c". The head 3 can pass through the narrowing portion 54b', which widens due to the slits 55', until the head 3 is seated in the spherical portion 54a'. Because of the narrowing portion 54b', the head 3 is prevented or restricted from inadvertently being pushed out of the head receiving part 5" in the direction of the first and 5a once the head 3 is in the spherical portion 54a'.

Assembly and use is otherwise similar to that of the first embodiment, the main difference being that the bone anchoring element 1 can be introduced from the first end 5a of the head receiving part 5".

FIGS. 41a to 45d depict an alternate embodiment that largely corresponds to the embodiment depicted in FIGS. 1 to 4, in which a polyaxial bone anchoring device includes a bone anchoring element 1 in the form of a bone screw having a shank 2 with a threaded section, and a spherical segment-shaped head 3. The head 3 has a recess 4 for engagement with a tool. The bone anchoring device further includes a head receiving part 5" for receiving the head 3 of the bone anchoring element 1, and a locking ring 6" for receiving a rod 7, for example a spinal stabilization rod, and for connecting the rod 7 to the bone anchoring element 1. In addition, the bone anchoring device includes a cap 8" for securing the rod 7, and a locking element 9 in the form of a set screw for locking the rod 7 and the head 3 relative to the rest of the bone anchoring device.

The head receiving part 5" receives a screw head, for example, head 3, and mounts to or connects to the cap 8" using a slotted ring 5f. The shank 2 is configured to be set into or attached to a bone. The locking ring 6" mounts to the head receiving part 5" from the underside, for example, from end 5b, and exerts pressure against the head receiving part 5" to lock the head 3 of the screw 1 when the head 3 is inserted in the head receiving part 5".

Figure 42A:
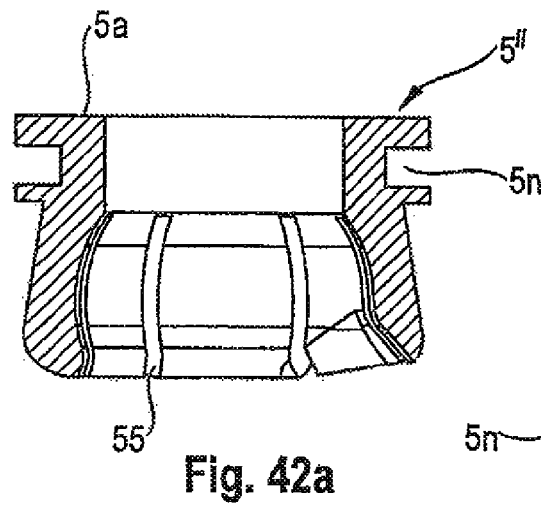
FIG. 42a shows a cross-sectional view of a head receiving part according to the embodiment of FIGS. 41a to 41c, the section being taken in a plane containing a central axis of the head receiving part.
Figure 42B:
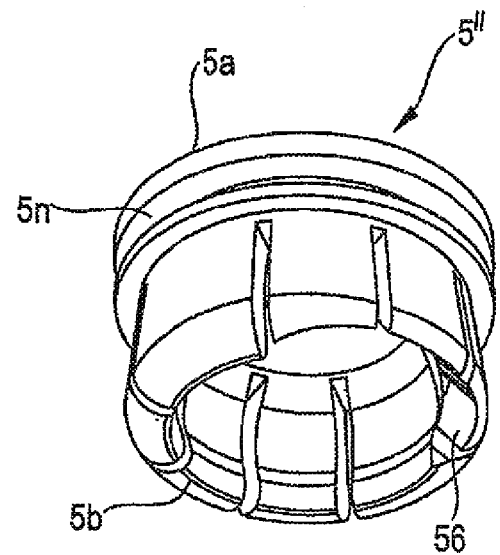
FIG. 42b shows a perspective view of the head receiving part of FIG. 42a from below.
Figure 42C:
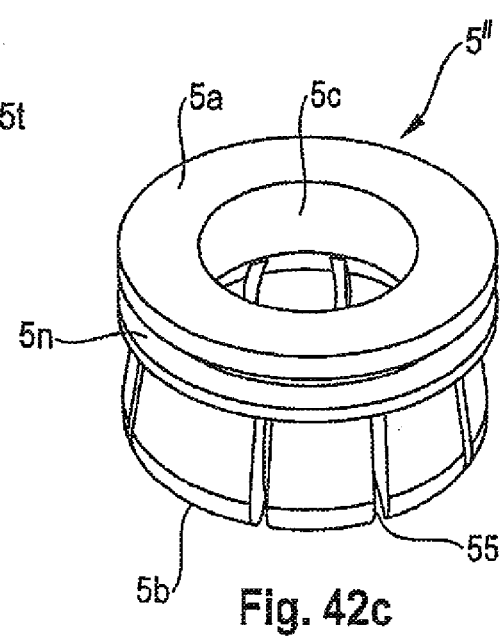
Figure 44A:
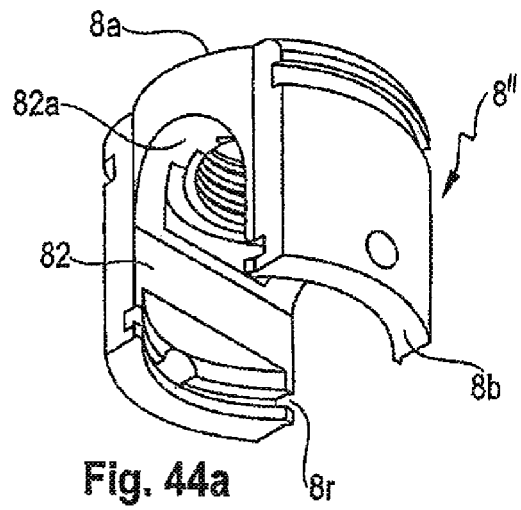
FIG. 44a shows a perspective view from a bottom of a cap of the polyaxial bone anchoring device according to FIGS. 41a to 41c.
Figure 44B:
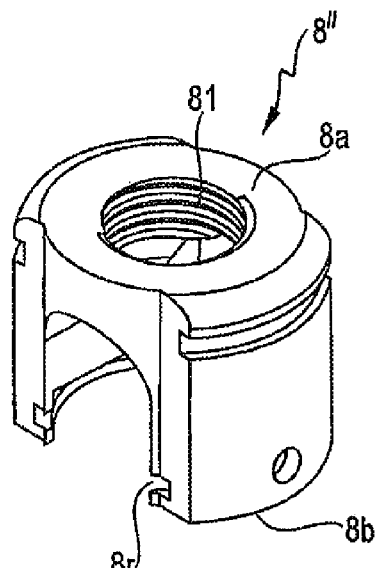
FIG. 44b shows a perspective view from a top of the cap of the polyaxial bone anchoring device according to FIGS. 41a to 41c.
Figure 44C:
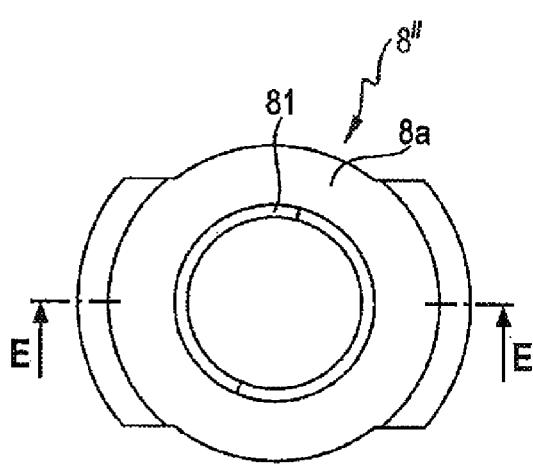
FIG. 44c shows a top view of the cap of FIGS. 44a and 44b.
Figure 44D:
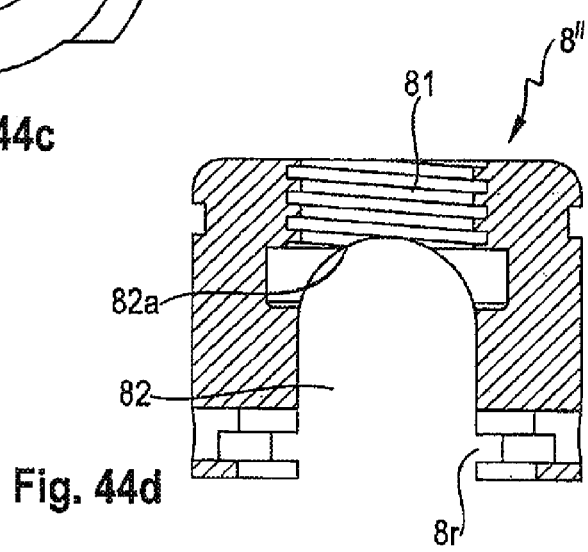
FIG. 44d shows a cross-sectional view of the cap of FIG. 44c, along line E-E in FIG. 44c.
Figure 45A:
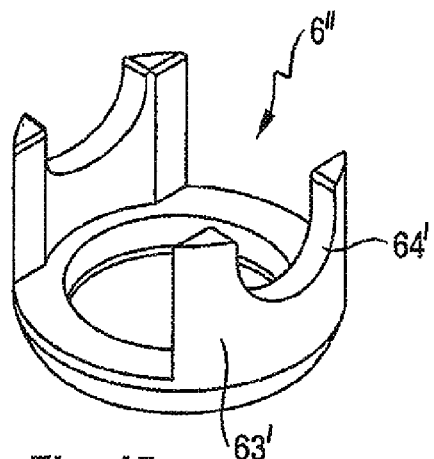
FIG. 45a shows a perspective view from a top of a locking ring of the polyaxial bone anchoring device according to FIGS. 41a to 41c.
Figure 45B:
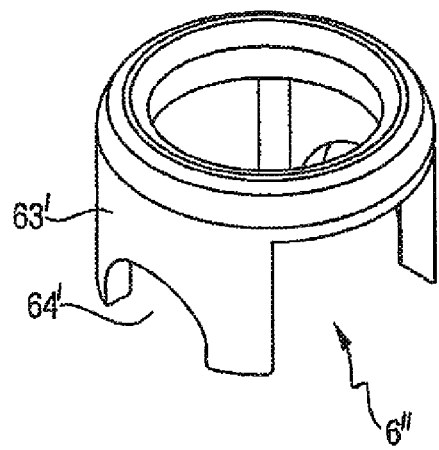
FIG. 45b shows a perspective view of a bottom of the locking ring of the polyaxial bone anchoring device according to FIGS. 41a to 41c.
Figure 45C:
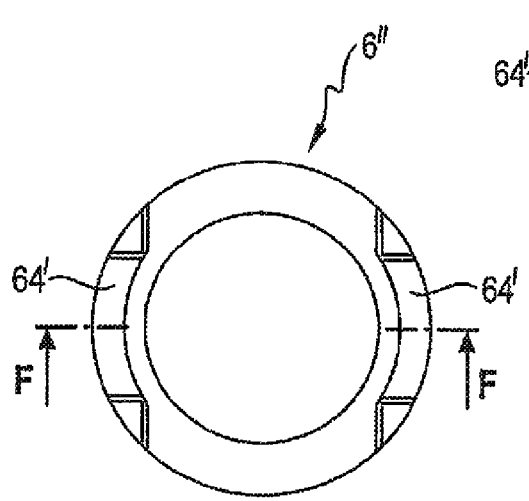
FIG. 45c shows a top view of the locking ring of FIGS. 45a and 45b.
Figure 45D:
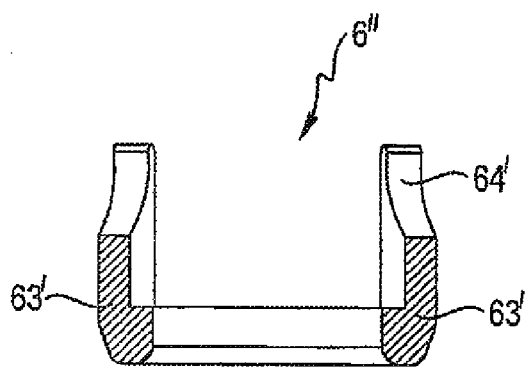
FIG. 45d shows a cross-sectional view of the locking ring of FIG. 45c, along line F-F in FIG. 45c.

Referring now to FIGS. 42a to 42c, the head receiving part 5" is further described below. As shown in FIGS. 42a and 42b, the head receiving part 5" may facilitate a larger pivot angle at a particular location or position, similarly as described above. An annular groove or notch 5n is formed near a first end 5a of the head receiving part 5". The slotted ring 5f is adapted to fit around or in the annular groove or notch 5n by deflecting or expanding a slot on the ring 5f. Once mounted around the annular groove 5n, the slotted ring 5f is capable of providing tension force against a corresponding annular notch or groove in the cap 8", to mount the head receiving part 5" within or to the cap 8".

While the head receiving part 5" is described as facilitating a larger pivot angle at a particular position, the features of the present embodiment, such as use of the slotted ring 5f to provide tension force between the head receiving part 5" and the cap 8", may also be implemented where the head receiving part 5" does not facilitate a larger pivot angle at a particular position, such as when a planar, annular edge is formed on the second end 5b of the head receiving part 5".

Referring now to FIGS. 44a to 44d, the cap 8" in the alternate embodiment will now be described, and compared to the cap 8 in the first embodiment. The cap 8" has near its second end 8b an annular notch or groove 8r for accommodating a portion of the slotted ring 5f. Whereas in the first embodiment, the cap 8 has a slit or slits 87 to allow the cap 8 to expand, in the present alternate embodiment, slits are not needed, because the tension force between the cap 8" and the head receiving part 5" is provided by the slotted ring 5f. Alternatively, use of the slotted ring 5f may reduce a number of slits implemented, for example, having one slit instead of two slits.

Figure 43:
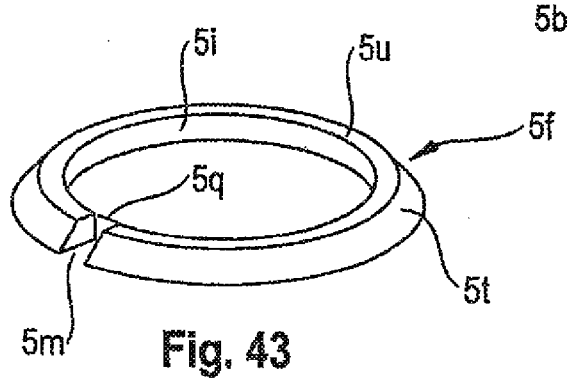
FIG. 43 shows a perspective view of a slotted ring according to the embodiment of FIGS. 41a to 41c.

Referring now to FIG. 43, an embodiment of the slotted ring 5f is described. The slotted ring 5f has a vertical inner edge 5i, a downwardly sloping outer edge 5t, and an upper side 5u that is substantially parallel to a lower side 5m. The slot 5q enables the ring 5f to expand to be mounted around or into the annular groove 5n of the head receiving part 5", so that the ring 5f may provide restraining force against the annular groove 8r of the cap 8" when the head receiving part 5" and the cap 8" are assembled together.

Referring to FIGS. 41a and 41c, a cross-sectional shape of the slotted ring 5f may be trapezoidal, as shown, with the outer edge 5t of the ring 5f sloping outwardly and downwardly (i.e., in a direction of the head 3 or second end 5b of head receiving part 5") when mounted. An angle of the sloping outer edge 5t may be approximately 45° with respect to a central axis C of the assembly, for example. The inner edge 5i of the ring 5f may be at substantially right angles to the top 5u and bottom 5m of the ring 5f forming the trapezoid, and substantially parallel to the central axis C when mounted.

Referring now to FIGS. 41a and 45a to 45d, the locking ring 6" may be optimized for stability and strength. For example, sidewalls of a recess 64' may be thickened and thereby made more stable, as compared to previous embodiments. That is, walls of the locking ring 6" may be made thicker in various regions that may be more crucial or critical strength points.

Furthermore, referring again to FIGS. 41a to 41c, in the alternate embodiment, the slotted ring 5f mates with an annular groove or notch 5n in a section of the head receiving part 5" positioned away from an inserted head 3. The slotted ring 5f therefore serves to provide tension force between the receiving part 5" and the annular notch or groove 8r in the cap 8", near an end 5a that receives the rod 7. Furthermore, the slotted ring 5f expands into notch or groove 8r upon assembly so that the ring 5f holds together the cap 8" and the head receiving part 5".

In some embodiments, the ring 5f may be placed first in the annular groove 5n of the head receiving part 5", and the parts may be provided, for example, to a practitioner in a preassembled manner. The locking ring 6" may also be pre-assembled around the head receiving part 5". During operation, the rod 7 is inserted into the recesses 64' of the locking ring 6". Then, the cap 8" is placed onto the head receiving part 5", where the slanted surface 5t of the ring 5f is oriented such that the cap 8" is able to slide downward over the ring 5f to mate with the head receiving part 5". As shown in FIG. 41c, the ring 5f expands into the groove 8r of the cap 8" upon assembly, in order to hold the cap 8" and the head receiving part 5" together.

While in the alternate embodiment described above, the slotted ring 5f is depicted as having a trapezoidal cross-section, rings with other cross-sectional shapes are also possible, such as rings having a circular, elliptical, or otherwise curved outer edge, for example. Similarly, the inner edge of the slotted ring may also have a different cross-sectional shape, such as a circular, elliptical, or otherwise curved shape, for example.

The shape of the annular groove or notch 5n may be a square or rectangular notch as shown, for example, to mate with the square shape of the inner edge 5i of the ring 5f. However, it is also possible for the annular groove or notch 5n to have various different shapes, such as trapezoidal or triangular, for example, in order to favorably or readily mate with a differently shaped ring in a corresponding fashion.

The foregoing alternative embodiment may provide for a cap, locking ring, and entire bone anchoring device that is made to be more stable or sturdy.

It shall also be understood that the second embodiment and further embodiments of the bone anchoring device may also be designed as a top loading bone anchoring device. In such a modification the head receiving part may be shaped like the head receiving part 5" in the third embodiment with respect to its hollow interior portion for receiving the head 3.

Various other modifications may also be conceivable. For example the configuration of the locking ring and the cooperating outer surface portion of the head receiving part can be in other manners designed. For example, an inner surface of the locking ring may be tapered to cooperate with a tapered outer surface of the head receiving part. Or, an outer surface portion of the head receiving part may be convexly rounded, while an inner surface of the locking ring may be straight or tapered. The cooperating surfaces of the locking ring and the head receiving part can also be parallel, so that the clamping of the head is achieved by an interference fit between the locking ring and the head receiving part.

For the bone anchoring element, various bone anchoring elements can be used that differ with respect to their shank lengths, diameters, or thread forms, or the bone anchoring elements may have through channels. Also, hooks, nails, or any other anchoring elements may also be utilized.

To facilitate the enlarged pivot angle, it may also be possible to use a head receiving part that has been cut at a bottom end in an inclined manner, so as to generate an enlarged pivot angle or a larger circumferential area. The recessed area can also be formed by a cut-out in an otherwise symmetrical head receiving part that provides an opening transverse to the central axis C.

In some embodiments, the rod receiving recess can also be semi-circular, quarter-circular, or U-shaped, or can have any shape that is configured to accommodate a rod therein.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
   a bone anchoring element having a shank for anchoring to a bone and a head;
   a head receiving part having an open first end, an open second end with a bounding edge, and a hollow interior portion in communication with the open first end and the open second end for receiving the head therein, the head receiving part being flexible for clamping the head; and
   a locking ring having a first end, a second end, and a rod receiving portion defining a recess for receiving a rod at the first end, wherein the recess has a greatest horizontal width at a first region spaced apart from the first end of the locking ring, and wherein a horizontal width of the recess narrows from the first region in a direction towards the first end of the locking ring;
   wherein the locking ring is configured to engage and be positioned around the head receiving part, and wherein when the locking ring is around the head receiving part, the engagement prevents separation of the locking ring from the head receiving part; and
   wherein when the head is in the head receiving part with the shank extending through the open second end of the head receiving part and the locking ring is around the head receiving part, the locking ring is movable from a first position wherein the head is pivotable in the head receiving part and the locking ring is rotatable relative to the head receiving part, to a second position wherein the first end of the locking ring is positioned closer to the second end of the head receiving part and wherein the locking ring applies a compressive force to the head receiving part to lock an angular position of the bone anchoring element and a rotational position of the locking ring relative to the head receiving part.

2. The bone anchoring device of claim 1, wherein when the head is in the head receiving part, the open second end of the head receiving part is configured to permit the bone anchoring element to pivot at a larger maximum pivot angle at a first location of the bounding edge than at a second location of the bounding edge.

3. The bone anchoring device of claim 2, wherein the bounding edge has a recessed area that facilitates an enlarged pivot angle for the bone anchoring element.

4. The bone anchoring device of claim 1, wherein the head receiving part comprises a portion with an outer surface that has a smallest diameter nearest the first end and a diameter that increases towards the open second end.

5. The bone anchoring device of claim 1, wherein the head receiving part comprises a wall with a plurality of slits.

6. The bone anchoring device of claim 1, wherein the head has a spherical segment-shaped outer surface and the head receiving part defines a spherical segment-shaped seat portion for accommodating the head.

7. The bone anchoring device of claim 6, wherein the head receiving part has a through hole at the first end with a diameter smaller than a greatest diameter of the head.

8. The bone anchoring device of claim 6, wherein the head receiving part has a bore at the first end with a diameter greater than the diameter of the head, and wherein between the bore and the seat, a narrowing portion is provided that is configured to expand when the head is inserted through the first end.

9. The bone anchoring device of claim 1, wherein the locking ring comprises two projections diametrically opposite to each other, the projections each having a recess configured for inserting a rod and for preliminarily holding the inserted rod therein.

10. The bone anchoring device of claim 9, wherein the recess has a circle segment-shaped contour defining more than half of a circle.

11. The bone anchoring device of claim 1, further comprising a cap configured to be connected to the head receiving part.

12. The bone anchoring device of claim 11, wherein the head receiving part comprises a first portion adjacent to the first end comprising an undercut for engagement with the cap.

13. The bone anchoring device of claim 11, wherein the head receiving part has a groove for engagement with the cap.

14. The bone anchoring device of claim 11, wherein the cap has a first end configured to face the head receiving part, a second end opposite thereto, and two diametrically opposite recesses for a rod to pass through.

15. The bone anchoring device of claim 11, wherein the cap has a threaded through hole, and wherein a locking element configured to extend from the cap to engage an inserted rod comprises a set screw configured to be accommodated in the through hole.

16. The bone anchoring device of claim 11, wherein the cap comprises a side wall having at least one axial slit to render the cap flexible in a radial direction.

17. The bone anchoring device of claim 11, wherein the cap comprises a circumferential projection with an undercut portion for engagement with a portion of the head receiving part.

18. A modular polyaxial bone anchoring device system comprising:
   at least two bone anchoring elements each having a shank for anchoring to a bone and a head, wherein at least two of the bone anchoring elements are shaped differently;
   a head receiving part having an open first end, an open second end with a bounding edge, and a hollow interior portion in communication with the open first end and the open second end for receiving the head of one of the bone anchoring elements therein, the head receiving part being flexible for clamping the head; and a locking ring having a first end, a second end, and a rod receiving portion defining a recess for receiving a rod at the first end, wherein the recess has a greatest horizontal width at a first region spaced apart from the first end of the locking ring, and wherein a horizontal width of the recess narrows from the first region in a direction towards the first end of the locking ring;

wherein the locking rinq is configured to engage and be positioned around the head receiving part, and wherein when the locking ring is around the head receiving part, the engagement prevents separation of the locking ring from the head receiving part;

wherein when the head of one of the bone anchoring elements is in the receiving part with the shank extending through the open second end of the head receiving part and the locking ring is around the head receiving part, the locking ring is movable from a first position wherein the head is pivotable in the head receiving part and the locking ring is rotatable relative to the head receiving part, to a second position wherein the first end of the locking ring is positioned closer to the second end of the head receiving part and wherein the locking ring applies a compressive force to the head receiving part to lock an angular position of the bone anchoring element and a rotational position of the locking ring relative to the head receiving part; and wherein the bone anchoring elements are interchangeably connectable to the head receiving part.

19. The system according to claim 18, wherein when the head of one of the bone anchoring elements is in the head receiving part, the open second end of the head receiving part is configured to permit the bone anchoring element to pivot at a larger maximum pivot angle at a first location of the bounding edge than at a second location of the bounding edge.

20. The system according to claim 19, further comprising a second head receiving part with a first end and an open second end having a bounding edge, wherein the head receiving parts are configured to facilitate different maximum pivot angles from one another, and wherein the head receiving parts are interchangeably connectable with the bone anchoring elements.

21. The system according to claim 18, further comprising a cap configured to be connected to the head receiving part.

* * * * *

UNITED STATES PATENT AND TRADEMARK OFFICE
CERTIFICATE OF CORRECTION

PATENT NO. : 9,532,809 B2  
APPLICATION NO. : 14/822618  
DATED : January 3, 2017  
INVENTOR(S) : Lutz Biedermann et al.

Page 1 of 1

It is certified that error appears in the above-identified patent and that said Letters Patent is hereby corrected as shown below:

In the Claims

| | |
|---|---|
| Column 13, Line 8, | Delete "locking rinq is", |
| Claim 18 | Insert --locking ring is-- |

Signed and Sealed this  
Twenty-fourth Day of July, 2018

Andrei Iancu  
*Director of the United States Patent and Trademark Office*